United States Patent [19]

Van Winckel et al.

[11] 4,267,378
[45] May 12, 1981

[54] 2,2-DIALKOXY-6-CHLOROCYCLOHEXA-NONES

[75] Inventors: Carl E. Van Winckel, 1425 Sandhurst Pl., West Vancouver, British Columbia, Canada; David H. Dolphin, Vancouver, Canada; Elena Dumitrescu, Coquitlam, Canada; Kent F. Van Winckel, West Vancouver, Canada

[73] Assignee: Carl E. Van Winckel, West Vancouver, Canada

[21] Appl. No.: 54,035

[22] Filed: Jul. 2, 1979

Related U.S. Application Data

[63] Continuation-in-part of Ser. No. 713,784, Aug. 12, 1976, abandoned, and Ser. No. 802,181, May 31, 1977, Pat. No. 4,166,914.

[51] Int. Cl.³ .......................................... C07C 49/403
[52] U.S. Cl. ..................................................... 568/376

[58] Field of Search ...................... 260/586R; 568/376

[56] References Cited

U.S. PATENT DOCUMENTS

| Re. 29,201 | 5/1977 | McKague et al. ........... 260/586 R X |
| 3,931,324 | 1/1976 | Rosenthal et al. ............... 260/586 R |
| 3,992,452 | 11/1976 | McKague et al. ............... 260/586 R |
| 4,166,914 | 9/1979 | Van Winckel et al. ..... 260/586 R X |

*Primary Examiner*—Bernard Helfin
*Attorney, Agent, or Firm*—Edward B. Gregg

[57] ABSTRACT

O-alkoxyphenols are produced from cyclohexanone or cyclohexanol by chlorination of cyclohexanone or cyclohexanol to trichlorocyclohexanone and reaction of the trichlorocyclohexanone with an aliphatic, monohydric alcohol having one to four carbon atoms and a base to form an intermediate compound or compounds which are further reacted to convert the intermediate compound or compounds to an o-alkoxyphenol.

3 Claims, No Drawings

2,2-DIALKOXY-6-CHLOROCYCLOHEXANONES

CROSS REFERENCE TO RELATED APPLICATION

This application is a continuation-in-part of application Ser. No. 713,784 filed Aug. 12, 1976, entitled "Production of Alkoxyphenols" now abandoned and is a division of application Ser. No. 802,181 filed May 31, 1977 now U.S. Pat. No. 4,166,914.

BACKGROUND OF THE INVENTION

1. Field of the Invention

This invention relates to the production of o-alkoxyphenols from cyclohexanol, cyclohexanone or trichlorocyclohexanone and to new chemical compounds.

2. Prior Art Relating to the Disclosure

Known processes for the production of o-alkoxyphenols are either costly or their production is accompanied with isomers which are difficult to separate. U.S. Pat. No. 3,819,719 describes a process for the production of o-alkoxyphenols from cyclohexanone by (1) chlorination of cyclohexanone to chlorocyclohexanone, (2) conversion of the chlorocyclohexanone to an alkoxycyclohexanone, and (3) dehydrogenation of the alkoxycyclohexanone with a Group VIII noble metal catalyst to the corresponding o-alkoxyphenol. On scale up of the process described in the aforementioned patent to commercial production, appreciable amounts of by-products are produced which are difficult to recover. The process also requires a relatively large amount of energy which, at today's cost, is uneconomical.

Processes for the production of o-alkoxyphenols from o-chloronitrobenzene are known but are expensive. Production of o-alkoxyphenols from catechol is also known but is fraught with problems of product separation and purification.

U.S. Pat. No. 3,894,087 describes a method of producing 2,2,6-trichlorocyclohexanone from cyclohexanone and lower α-chlorinated cyclohexanones which, when pyrolyzed, provides isomerically pure o-chlorophenol.

SUMMARY OF THE INVENTION

It is a primary object of this invention to provide a process for the production of o-alkoxyphenols by reaction of trichlorocyclohexanone with an aliphatic, monohydric alcohol having from 1 to 4 carbon atoms and a base.

An additional object of this invention is to provide a process for the production of o-alkoxyphenols starting with cyclohexanone or cyclohexanol.

An additional object of this invention is to provide a process for the preparation of o-alkoxyphenols from trichlorocyclohexanone, cyclohexanone or cyclohexanol without the concurrent production of appreciable amounts of chlorophenol.

An additional object of this invention is to provide a process for the production of o-alkoxyphenols by reaction of trichlorocyclohexanone with an excess of an aliphatic, monohydric alcohol having from 1 to 4 carbon atoms and a base to form an intermediate compound which is heated in the presence of the same or a different base to a temperature sufficient to convert the intermediate compound to the corresponding o-alkoxyphenol.

An additional object of this invention is to provide a process for the production of dialkoxychlorocyclohexanone or trialkoxycyclohexanone compounds by reaction of trichlorocyclohexanone with an excess of an aliphatic monohydric alcohol having from 1 to 4 carbon atoms and a suitable base.

Another object of this invention is to provide a process for the conversion of a dialkoxychlorocyclohexanone compound to the corresponding o-alkoxyphenol by reaction of the compound with an organic base and heat.

An additional object of this invention is to provide a process for the production of o-alkoxyphenols such as guaiacol and guaethol from cyclohexanone or cyclohexanol by (1) chlorination of cyclohexanone or cyclohexanol contained in an inert solvent in the presence of a trialkylamine hydrochloride catalyst to yield trichlorocyclohexanone, (2) reacting the trichlorocyclohexanone with an aliphatic, monohydric alcohol such as methanol or ethanol and an organic or inorganic base or mixtures thereof to convert the trichlorocyclohexanone to dimethoxy- or diethoxychlorocyclohexanone and (3) heating the mixture containing the dimethoxy- or diethoxychlorocyclohexanone in the presence of an organic base for conversion to guaiacol or guaethol.

These and other objects are accomplished by (1) chlorination or cyclohexanol of cyclohexanone to trichlorocyclohexanone, and (2) reaction of the trichlorocyclohexanone with an excess of an aliphatic, monohydric alcohol having from 1 to 4 carbon atoms and a base to form an intermediate compound which, when heated with the same or a different base, is converted to an o-alkoxyphenol.

DESCRIPTION OF THE PREFERRED EMBODIMENTS

The starting material for production of the o-alkoxyphenols described herein may be cyclohexanol, cyclohexanone or trichlorocyclohexanone. Trichlorocyclohexanone (2,2,6-trichlorocyclohexanone) is prepared by chlorination of cyclohexanol, cyclohexanone or α-chlorinated cyclohexanones or mixtures thereof preferably in a suitable solvent or diluent therefor. Organic solvents which do not react appreciably with chlorine and which are inert with respect to the trichlorocyclohexanone and HCl may be used such as acetic acid, 1,1,1-trichloroethane, chlorobenzene or carbon tetrachloride. α-chlorinated cyclohexanones are also useful as solvents. The cyclohexanone, with or without additional amine, may be added continuously to the chlorination mass which may or may not be diluted with an inert solvent. If the chlorination is carried out in the presence of an organic base, such as a trialkylamine, the amine should be converted to the amine hydrochloride before addition of either chlorine or the cycloaliphatic reactants or added slowly to insure a considerable excess of HCl throughout. Chlorination of cyclohexanone or cyclohexanol is carried out by contact with chlorine at a relatively low temperature such as 0°–60° C. The reaction is preferably carried out until more than 90% trichlorocyclohexanone is obtained along with some di-, and tetra-chlorocyclohexanone. The trichlorocyclohexanone may be recovered by distillation or used directly in the next reaction.

Trichlorocyclohexanone can be converted to an intermediate dialkoxychlorocyclohexanone compound (2,2-dialkoxy-6-chlorocyclohexanone) by reaction with an alcohol in the presence of a base, preferably in a substantially non-aqueous system. The base used may be an inorganic or organic base. The dialkoxy compound is then converted to the corresponding o-alkoxyphenol by heating the dialkoxy compound in the presence of additional base. The conversion of trichlorocyclohexanone to an o-alkoxyphenol involves complex, competing chemical reactions with effective yields of the o-alkoxyphenol obtained dependent on the base or combination of bases used and the reaction conditions. Strong bases, such as sodium hydroxide and sodium methylate, tend to favor formation of trialkoxycyclohexanone compounds which, when heated in the presence of the base, yield the corresponding o-alkoxyphenol. Weaker bases, such as organic amines, alkali or alkaline earth carbonates, and alkaline earth oxides tend to favor formation of the dialkoxychlorocyclohexanone compound which is then converted to the corresponding o-alkoxyphenol. The presence of water in the reaction mixture favors the formation of 3-chloro-1,2-cyclohexanedione which is not desired.

The reaction sequence may be illustrated as follows:

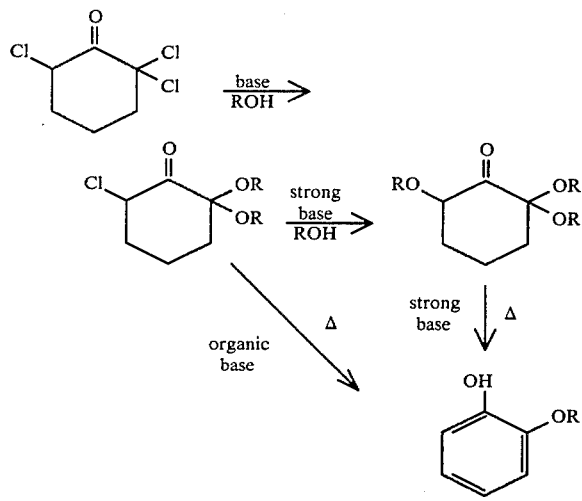

The intermediate dialkoxychlorocyclohexanone is formed by addition of a suitable base to a solution of trichlorocyclohexanone in an excess amount of an aliphatic, monohydric alcohol having 1 to 4 carbon atoms. This reaction can be carried out in various ways but in general yields increase with: (1) increasing dilution of both the trichlorocyclohexanone and the base in the alcohol, (2) lower temperature in the range of 10° C. to 30° C. (although a range of −10° C. to 90° C. is possible, preferably below 60° C.) and a pH of below 11 (preferably in the range of 7.0 to 8.5). Increasing concentration of amine or higher pH favor the formation of chlorophenol. The presence of water causes the formation of 3-chloro-1,2-cyclohexanedione. Usually the base is added gradually to the trichlorocyclohexanone in alcohol, however, it is possible to add the trichlorocyclohexanone and the base to the alcohol concurrently. Bases which are soluble in alcohol are usually diluted with the alcohol before addition. Relatively insoluble solid bases such as Na$_2$CO$_3$ may be added all at once. The optimum procedure also varies depending on which alcohol is used.

Suitable bases which can be employed for the production of the dialkoxychlorocyclohexanone from trichlorocyclohexanone include tertiary amines wherein the primary or secondary alkyl groups have from 1 to 8 carbon atoms such as trimethylamine, N,N,N',N'-tetraethylethylenediamine, N,N,N',N'-tetramethyl-1,4-butanediamine, N,N-dimethylbenzylamine, N-ethylpiperidine, N-ethylmorpholine; alkylated aromatic amines such as N,N-dimethylaniline; amines such as pyridine and its derivatives, i.e. methyl pyridine; or inorganic bases such as alkali or alkaline earth carbonates, oxides, hydroxides or alkoxides and mixtures of organic and inorganic bases. Calcium carbide, which also functions as a base, may be used.

If an excess of a strong base, such as sodium hydroxide or sodium methylate is used (three equivalents relative to the trichlorocyclohexanone), trialkoxycyclohexanone and other compounds free of any chlorine are formed. The trialkoxycyclohexanone compounds may be converted to the corresponding o-alkoxyphenol by the addition of one or more additional equivalents of the strong base, relative to the trialkoxycyclohexanone compound, to the reaction mixture which is then heated to 80° C. to 200° C., preferably 100° C. to 150° C. to form the corresponding o-alkoxyphenol. The process may be carried out under pressure although the pressure requirements can be markedly reduced or eliminated by distilling off part of the alcohol or adding appropriate diluents.

The conversion of the dialkoxychlorocyclohexanone to the corresponding o-alkoxyphenol is carried out by heating a solution of the dialkoxychlorocyclohexanone compound in the presence of an organic base from about 120° C. to about 250° C. The reaction may be carried out in the presence of some of the excess alcohol used to prepare the dialkoxychlorocyclohexanone but the alcohol is preferably removed prior to the reaction. One or more equivalents, relative to the dialkoxychlorocyclohexanone, of a base, such as an organic trialkylamine soluble in the essentially non-aqueous reaction mixture, is added to the reaction mixture containing the dialkoxychlorocyclohexanone for conversion. An excess of base does not appear to be detrimental. The reaction may be carried out at or above atmoshpheric pressure depending whether or not most of the excess alcohol is distilled off. The bases used for the conversion of the dialkoxychlorocyclohexanone to o-alkoxyphenyl include tertiary amines wherein the primary or secondary alkyl groups have from 1 to 8 carbon atoms such as trimethylamine, N,N,N',N'-tetraethylethylenediamine, N,N,N',N'-tetramethyl-1,4-butanediamine, N,N-dimethylbenzylamine, N-ethylpiperidine, N-ethylmorpholine; alkylated aromatic amines such as N,N-dimethylaniline; amines such as pyridine and its derivatives, i.e. methyl pyridine; or others. The choice of the organic base employed depends on its boiling point, solubility in the reaction mixture, ease of recovery for reuse and other factors. The organic base may be buffered with a suitable acid such as acetic acid. The use of an appropriate buffer appears to reduce the temperature necessary to carry out the reaction.

The o-alkoxyphenol in the reaction mixture is recovered by suitable means. The base also may be recovered for reuse.

If trichlorocyclohexanone is reacted with an aliphatic, monohydric alcohol in the presence of a base in one step at temperatures above 100° C. some o-alkoxyphenol is obtained, however the major reaction product is chlorophenol.

Satisfactory yields of the intermediate dialkoxychlorocyclohexanone compound from trichlorocyclohexanone can be obtained using inorganic bases such as sodium carbonate and/or calcium oxide particularly if, in those instances where an amine hydrochloride is used during chlorination, the amine hydrochloride is removed from the trichlorocyclohexanone before the addition of the sodium carbonate and/or calcium oxide. The dilution of the trichlorocyclohexanone with alcohol before the addition of the base is less when using sodium carbonate and/or calcium oxide than when using an organic amine as the base.

The following examples are illustrative of the process claimed:

EXAMPLE 1

Trichlorocyclohexanone was prepared by mixing 530 cc. cyclohexanone and 3 liters acetic acid in a 5 liter 3 neck flask equipped with magnetic stirrer, condenser (connected to a trap for HCl formed), thermometer and sparger for chlorine. While chlorine was sparged into the mixture of cyclohexanone and acetic acid the temperature was kept under 50° C. After 7½ hours the reaction was complete. The acetic acid was distilled off at reduced pressure and reused. Analysis of the reaction mixture by GLC showed about 92% trichlorocyclohexanone.

The stripped trichlorocyclohexanone can be used directly for the preparation of an o-alkoxyphenol.

EXAMPLE 2

5 gm of trichlorocyclohexanone and 5 gm of ethyl alcohol were mixed and added dropwise to a well agitated mixture of 10 gm. triethylamine and 22.5 gm. ethyl alcohol in a 100 ml. flask. The temperature was maintained below 15° C. A sample was taken and put in a glass pressure vessel and heated to 210° C. for 25 minutes. GLC analysis showed 83% chlorophenols, and 17% o-ethoxyphenol.

EXAMPLE 3

10 gm. of trichlorocyclohexanone and 30 gm. of ethyl alcohol were put in a flask equipped with a magnetic stirrer and thermometer. Twelve gm. of triethylamine were added dropwise, keeping the temperature of the reaction mixture between 0° C. to 5° C. When analysis by GLC showed an absence of trichlorocyclohexanone, a sample was taken and heated in a glass pressure vessel for 35 minutes at 215° C. GLC analysis showed two primary peaks; chlorophenol—21% and o-ethoxyphenol—65%.

EXAMPLE 4

20 gm. of trichlorocyclohexanone, 100 gm. ethyl alcohol and 20 gm. of sodium carbonate were mixed in a flask and brought up to reflux. After 1½ hours, analysis by GLC indicated the presence of diethoxychlorocyclohexanone. The solution was cooled, the salts were filtered off and the intermediate diethoxychlorocyclohexanone was recovered for use in Example 5.

EXAMPLE 5

To the diethoxychlorocyclohexanone of Example 4, one equivalent of triethylamine relative to the diethoxy compound was added and the mixture placed in a glass pressure vessel and heated at 200° C. for 30 minutes. GLC analysis indicated conversion to o-ethoxyphenol.

EXAMPLE 6

Ten gm. of tributylamine, 5 gm of dimethoxychlorocyclohexanone and 2 gm. of veratrole were charged to a glass pressure tube and heated to 200° C. for half an hour in an oil bath. On cooling the tributylamine hydrochloride was neutralized with sodium carbonate, the salt filtered off and the filtrate distilled. Analysis of the distillate by GLC showed a yield of guaiacol equal to 70% of theory and a chlorophenol content equaling 3% of the guaiacol.

EXAMPLE 7

A mixture of 1.0 mole of dimethoxychlorocyclohexanone, 1.1 mole of N,N,N',N'-tetramethyl-1,4-butanediamine and 2.3 mole acetic acid as a buffer were heated in a glass pressure vessel to 200° C. for ½ hour. The amine hydrochloride produced was neutralized with sodium acetate. A sample of the reaction mixture was analyzed by GLC analysis and showed a yield of guaiacol approximating 90% of theory and 2% chlorophenol.

EXAMPLE 8

A mixture of 6.0 ml. of 88% dimethoxychlorocyclohexanone and 8.3 ml. of triethylamine were reacted as in the previous example. GLC analysis showed a theoretical yield of guaiacol based on the dimethoxychlorocyclohexanone contained in the mixture.

EXAMPLE 9

To 1.9 gm. of dimethoxychlorocyclohexanone in 5 ml. methanol was added 0.58 gm. of sodium methoxide (as a 23% solution in methanol) dropwise with good agitation at 20° C. to 30° C. To this reaction mixture was then added 1.6 gm. of 25% caustic soda all at once. The resulting mixture was heated in a pressure vessel to 140° C. for ½ hour. After cooling, it was neutralized with concentrated HCl. GLC analysis indicated the reaction mixture contained 57% guaiacol and 7% chlorophenol.

EXAMPLE 10

Guaiacol was prepared from cyclohexanone by mixing 95 cc. tripropylamine and 416 cc. methylene chloride. Anhydrous HCl was then added until the hydrochloride of tripropylamine was formed. 1 mole of cyclohexanone was added to the reaction mixture contained in a three neck flask equipped with mechanical stirrer, condenser, thermometer and sparger for chlorine. Chlorine was sparged into the mixture of cyclohexanone and tripropylamine while maintaining the temperature below 20° C. After approximately nine hours the reaction mixture was analyzed by GLC to contain 95% trichlorocyclohexanone; 2% dichlorocyclohexanone; and 2% tetrachlorocyclohexanone. Vacuum was applied from 3 to 5 minutes to remove excess HCl. The reaction mixture containing the trichlorocyclohexanone was then cooled to 10° C. and 2.6 moles tripropylamine added dropwise to the reaction mixture while keeping the pH of the mixture below 7.4 as follows:

0.6 mole as a 25% solution of tripropylamine in methanol;

1.0 mole as a 10% solution of tripropylamine in methanol;

0.9 mole as a 25% solution of tripropylamine in methanol;

0.1 mole neat tripropylamine.

The alcohol/tripropylamine solutions were added to the reaction mixture over a period of 6 hours for pH control. Analysis of the reaction mixture after reaction by GLC showed 96.8% dimethoxychlorocyclohexanone and 1.8% chlorophenol. To the reaction mixture was added 1.5 equivalents of tripropylamine. The mixture was then distilled at a pot temperature of 70° C. to 100° C. and a head temperature of 20° C. to 64° C. until all the methylene chloride and most of the methanol was removed. The pot temperature was then increased to 170° C. In approximately 20 minutes the reaction was complete. Analysis by GLC showed: 93.2% guaiacol and 3.9% chlorophenol.

EXAMPLE 11

To 66 ml. of a chlorination mass prepared as in Example 10 and containing 0.1 mole trichlorocyclohexanone was added 33 ml. methanol. The mixture was cooled to 10° C. and a 25% solution of sodium methylate in methanol added until the pH reached 6.0. Two additional equivalents (0.2 mole) relative to the trichlorocyclohexanone of a 25% solution of sodium methylate in methanol were then added at or below 10° C. and at or below pH 7.5 over a five hour period of time. The salt formed was removed by filtering and the methanol distilled off to a pot temperature of 80° C. Then 0.12 mole of tripropylamine was added and the heating continued to distill off more methanol and some solvent up to a pot temperature of 155° C. The reaction was complete in 30 minutes after the addition of the tripropylamine. Analysis by GLC showed more than 90% guaiacol and 3.5% chlorophenol. The yield of the intermediate dimethoxychlorocyclohexanone from trichlorocyclohexanone using sodium methylate is improved by the presence of the tripropylamine hydrochloride in the trichlorocyclohexanone reaction mixture (as described in the first part of Example 10) over the yield obtained when using sodium methylate alone. It is believed that sodium methylate reacts almost instantaneously with the tripropylamine hydrochloride to yield tripropylamine in a sufficiently dilute form to avoid the undesirable production of chlorophenol.

EXAMPLE 12

In a three or four neck flask equipped with a magnetic stirrer, thermometer, liquid addition tube extending below the surface of the liquid, pH probe, a gas addition tube and a water bath, was placed 250 ml of methanol. The temperature was adjusted to approximately 33° C. and 102 ml of chlorination product containing approximately 0.5 mole of trichlorocyclohexanone was added dropwise through the liquid addition tube over 4 hours. At the same time trimethylamine gas was added above the surface at a rate to maintain the pH between 5.5 and 6.0. After the trichlorocyclohexanone was added, the amine addition was continued until the pH reached 6.8. Stirring was continued for several hours at which time a GLC showed a yield of dimethoxychlorocyclohexanone of approximately 90% and less than 5% chlorophenol.

We claim:

1. 2,2-Dialkoxy-6-chlorocyclohexanones in which the alkyls of the alkoxy groups are the same and contain one to four carbon atoms.
2. 2,2-Dimethoxy-6-chlorocyclohexanone.
3. 2,2-Diethoxy-6-chlorocyclohexanone.

* * * * *